United States Patent [19]

Birum

[11] 4,070,336
[45] Jan. 24, 1978

[54] HYDROGEN PHOSPHONATES AND POLYMER COMPOSITIONS CONTAINING THEM AS FLAME RETARDANTS

[75] Inventor: Gail H. Birum, Kirkwood, Mo.
[73] Assignee: Monsanto Company, St. Louis, Mo.
[21] Appl. No.: 720,323
[22] Filed: Sept. 3, 1976
[51] Int. Cl.$^2$ .......................... C07F 9/02; C08K 5/51; C08K 5/53
[52] U.S. Cl. .......................... 260/45.8 R; 260/927 R; 260/937
[58] Field of Search ............... 260/45.8 R, 927 R, 937

[56] References Cited

U.S. PATENT DOCUMENTS

| | | | |
|---|---|---|---|
| 2,957,856 | 10/1960 | Guest et al. | 526/225 |
| 3,966,849 | 6/1976 | Noetzel et al. | 260/45.8 R |
| 3,978,167 | 8/1976 | Albright | 260/927 R |
| 3,997,505 | 12/1976 | Albright | 260/45.8 R |

OTHER PUBLICATIONS

Sehring et al., Chem. Abs., 79, 115722k (1973).

*Primary Examiner*—Donald E. Czaja
*Assistant Examiner*—H. H. Fletcher
*Attorney, Agent, or Firm*—Herman O. Bauermeister

[57] ABSTRACT

The present invention relates to cyclic phosphorus compounds including cyclic hydrogen phosphonates and processes for the preparation thereof.

The present invention relates to an improved process for the preparation of cyclic hydrogenphosphonates, which comprises the reaction of phosphorochloridites with formic acid in accordance with the general reaction set forth below:

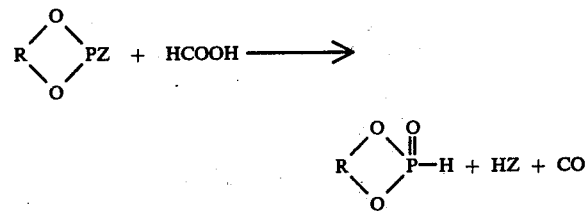

where R is an alkylene or haloalkylene group of a 1,2-glycol having from two to six carbon atoms, or a 1,3-glycol having from three to eight carbon atoms, and Z is Cl or Br. Ketone and sulfenyl derivatives are also a part of the present invention.

The cyclic phosphorus compounds are useful as flame retardants with organic polymers, such a polyurethanes, polyesters and polyamides.

23 Claims, No Drawings

HYDROGEN PHOSPHONATES AND POLYMER COMPOSITIONS CONTAINING THEM AS FLAME RETARDANTS

BACKGROUND OF THE INVENTION

The present invention relates to cyclic phosphorus compounds, such as cyclic hydrogenphosphonates, processes for the preparation of such compounds and their derivatives, and to flame retardant compositions containing the said cyclic phosphorus compounds.

Certain phosphonates have been employed as flame retardant additives, but have suffered from the defect of causing undesirable crosslinking of polymeric materials in which the phosphonates were employed. For example, the addition of such phosphonates to a molten polymer such as polyethylene terephthalate or a nylon, preliminary to the extrusion or spinning step has shown that the crosslinking prevents the formation of acceptable fibers. As a result of the crosslinking, the fibers contain lumps and irregular sections so that the extrusion through spinnerettes is hampered and the stretching, washing and other physical treatments of the fiber become impossible.

It has now however been found that certain cyclic phosphorus compounds including cyclic phosphonates are particularly useful as flame retardants for organic polymeric materials. The invention includes combinations of the present cyclic phosphorus compounds together with organic polymers such as polyurethanes, polyesters, e.g. polyethylene terephthalate, and polyamides e.g., the nylons.

SUMMARY OF THE INVENTION

The present invention relates to cyclic phosphonates such as cyclic hydrogenphosphonates and also to sulfenyl and ketone derivatives thereof.

The general formula for the cyclic phosphorus derivatives of the invention is:

$$\overset{O}{\underset{}{\overset{\parallel}{XPY}}}$$

where Y is selected from the group consisting of $$\begin{bmatrix} \diagup OCH_2 \diagdown \\ \phantom{xx} C(CH_2Br)_2 \\ \diagdown OCH_2 \diagup \end{bmatrix}$$

and $$\begin{bmatrix} \diagup OCH_2 \diagdown \phantom{x} \diagup CH_2O \diagdown \phantom{x} O \\ \phantom{xxx} C \phantom{xxxxxx} \overset{\parallel}{P}-X \\ \diagdown OCH_2 \diagup \phantom{x} \diagdown CH_2O \diagup \end{bmatrix}$$

and where X is selected from the group consisting of
—S(R$_c$)
where R is phenyl with 0 to 5 halogens, or phenyl with 0 to 2 nitro groups, or methyl with 0 to 3 chlorine atoms.
and $$\begin{array}{c} (R_d) \\ | \\ -C-OH \\ | \\ (R_d) \end{array}$$

where R$_d$ is an alkyl radical of 1 to 4 carbon atoms, or phenyl

The above compounds are derivatives of cyclic hydrogen-phosphontes. They are obtained by the reaction of a crude or purified hydrogenphosphonate with sulfenyl chlorides, or ketones, respectively.

Typical sulfenyl chlories include chlorophenyl sulfenyl chloride, and nitrophenylsulfenyl chloride, and bromophenylsulfenyl chloride, and 2,4-dinitrophenyl sulfenyl chloride, and chloromethylsulfenyl chloride, and trichloromethyl sulfenyl chloride.

Examples of ketones include acetone, methyl ethyl ketone, diethyl ketone, methyl propyl ketone, dibutyl ketone, and acetophenone.

The cyclic phosphorus compounds of the present invention including hydrogen phosphonates, are useful per se as flame retardant materials which provide phosphorus as a component to reduce flammability. Improvement in flame retardant properties results when hydrogen phosphonates are reacted with sulfenyl chlorides and ketones. Such resultant products do not burn readily, and instead inhibit flammability of an organic polymer, for instance a polyurethane which is useful in the production of an elastomer or a rigid or flexible foam. An example of an elastomeric polyurethane is the product obtained by heating together poly(tetramethylene ether) glycol and methylene bis(p-phenyl isocyanate).

The cyclic phosphorus compounds including the cyclic hydrogen phosphonates of the present invention are useful as flame retardant modifiers for organic polymers. These compounds can be added directly to the molten polymer or the components of a foam composition before polymerization, e.g. before spinning fibers or forming films or other shaped objects including foamed plastics. Typical polymers are polyesters, polyamides, polyurethanes, polyolefins, nitrile polymers such as polyacrylonitrile, vinyl polymers such as vinyl chloride, styrene polymers and copolymers such as acrylonitrile-butadiene-styrene compositions.

The general reaction of the process for the production of hydrogen phosphonates is based upon the use of formic acid with a phosphorohalidite, such as a phosphorochloridite, represented in the process below by the structure, $$R\begin{array}{c}\diagup O\diagdown\\ \phantom{x}\\ \diagdown O\diagup\end{array}PZ$$

where R is an alkylene, or haloalkylene group of a 1,2-glycol having from 2 to 8 carbon atoms, or of a 1,3-glycol having from 3 to 8 carbon atoms, and Z is Cl or Br. An example is:

$$HCOOH + R\begin{array}{c}\diagup O\diagdown\\ \phantom{x}\\ \diagdown O\diagup\end{array}PCl \longrightarrow R\begin{array}{c}\diagup O\diagdown\phantom{x}O\\ \phantom{x}\phantom{x}\overset{\parallel}{P}H\\ \diagdown O\diagup\end{array} + HCl + CO$$

Examples of specific useful phosphorochloridites are the bis(phosphorochloridites), such as 3,9-dichloro-2,4,8,10-tetraoxa-3,9-diphosphaspiro[5.5]undecane,

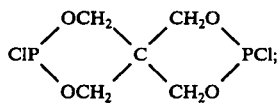

and the corresponding bromo derivative; 2-chloro-5,5-bis(bromomethyl)-1,3,2-dioxaphosphorinane,

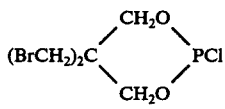

and the related phosphorochloridites, 2-chloro-5,5-dimethyl-1,3,2-dioxaphosphorinane, and 2-chloro-5-ethyl-5-methyl-1,3,2-dioxaphosphorinane, and 2-bromo-5,5-bis(chloromethyl)-1,3,2-dioxaphosphorinane, and 2-chloro-4-methyl-1,3,2-dioxaphosphorinane, and 2-chloro-5-phenyl-1,3,2-dioxaphosphorinane, and 2-chloro-5-(4-fluoro-3-bromophenyl)-1,3,2-dioxaphosphorinane.

The process of converting cyclic phosphorochloridites to cyclic hydrogen phosphonates can also be applied to five-membered ring phosphorochloridites, e.g., 4,5-dimethyl-2-chloro-1,3,2-dioxaphospholane, 2-chloro-1,3,2-dioxaphospholane, 2 butyl-1,3,2-dioxaphospholane, 4-chloromethyl-1,3,2-dioxaphospholane, and 4-methyl-1,3,2-dioxaphospholane.

The method of treating cyclic phosphorochloridites with formic acid provides an improved process for producing cyclic hydrogenphosphonates, sometimes called cyclic phosphities. Some earlier workers in this area of phosphorus chemistry have also called these compounds cyclic hydrogen phosphites, but preferable general terminology is to call these compounds cyclic hydrogenphosphonates because it better describes the predominant pentavalent state of the phosphorus. A number of methods are known for preparing cyclic hydrogenphosphonates, such as the use of triethylamine as an acid-binding agent in the hydrolysis of cyclic chlorophosphites (cyclic phosphorochloridites). In this procedure, an amine hydrochloride is produced as a by-product, and this must then be separated from the desired cyclic hydrogenphosphonate.

In the present improved process, using formic acid instead of water, the by-products are anhydrous hydrogen chloride and carbon monoxide, gaseous products which are easily removed, leaving easily isolated cyclic hydrogenphosphonate. For example, when attempts were made to prepare 3,9-H,3,9-dioxo-2,4,8,10-tetraoxa-3,9-diphosphaspiro[5.5]undedane(I).

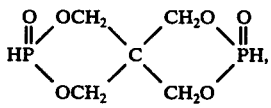

by treatment of 3,9-dichloro-2,4,8,10-tetraoxa-3,9-diphosphospiro[5.5]undecane with water by the prior art procedures, none of the desired product could be isolated from the mixture of side reaction products. However, when formic acid is used according to the present invention, essentially pure and easily isolated compound I is obtained.

Catalysts are unnecessary in the above process. A solvent is generally unnecessary when formic acid is used for conversion of cyclic phosphorochloridites to cyclic hydrogenphosphonates. Inert solvents or suspending liquids, e.g., acetonitrile, benzene and 1,2-dichloroethane, can however be used to aid mixing and temperature control.

The reaction is usually carried out by the addition of formic acid to the stirred phosphorochloridite at 10° to 100° C, preferably 30° to 70° C, while allowing the by-products hydrogen chloride (or hydrogen bromide) and carbon monoxide to be expelled through a condenser and then trapped or absorbed by suitable and safe methods such as neutralization. In one case, this mixture of gases is passed into a stirred suspension of aluminum trichloride and toluene to produce p-tolualdehyde by the Gatterman-Koch Reaction, thus confirming the composition of the effluent gases and demonstrating a practical by-product recovery application.

The hydrogenphosphonates are readily obtained by the admixing of formic acid with a phosphorochloridite as described above. Also, certain derivatives of the cyclic hydrogenphosphonates specifically cyclic phosphorus derivatives of sulfenyl chlorides and ketones, can be made. These derivatives have particular utility for fire retardancy purposes, as well as agricultural chemicals such as growth regulators and herbicides. In forming the derivatives, the above described reaction mixture may be used without the need of any separation step. However when desired the cyclic hydrogen phosphonate can be separated after its formation and used in a second step in order to form the said derivatives.

The process for the preparation of the said sulfenyl chloride and ketone derivatives is carried out at 10° to 100° C. No catalyst or solvent is necessary, although inert solvents such as benzene, toluene and chlorobenzene may be used.

The cyclic hydrogenphosphonates thus react with sulfenyl chlorides to give products that are useful as fire-retardants for organic polymers. An example is shown in the following equation.

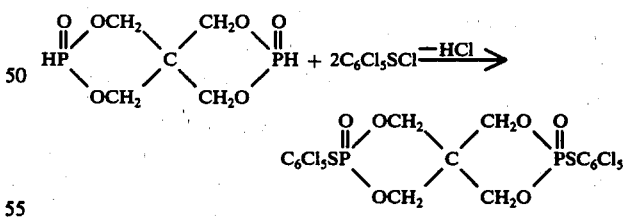

The sulfenyl chlorides have the formula $HSR_c$ where $R_c$ is phenyl with 0 to 5 halogens, or phenyl with 0 to 2 nitro groups, or methyl with 0 to 3 chlorine atoms.

Cyclic hydrogenphosphonates that can be produced according to the present invention will also react with low molecular weight ketones to produce new compounds that are useful as fire-retardant additives for organic polymers. A particularly convenient method for producing such products is to add formic acid to a mixture of the ketone and the cyclic phosphorochloridite in a one step reaction according to the following example:

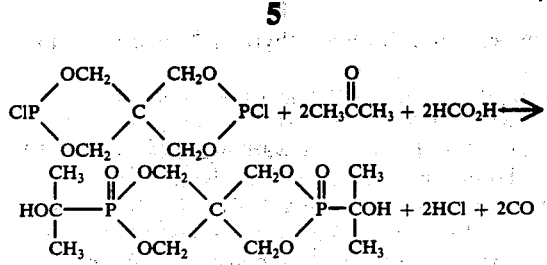

Examples of other ketones that can be used in this way are: methyl ethyl ketone, diethyl ketone, methylpropyl ketone, and acetophenone. The ketones have the formula

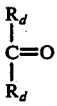

where $R_d$ is an alkyl radical of 1 to 4 carbon atoms or phenyl.

The compounds of the present invention are useful in flame-retardant materials. The method of testing flame-retardant properties is A.S.T.M. Designation D 2863-70, entitled "Standard Method of Test For Flammability of Plastics Using the Oxygen Index Method."

In the oxygen index (OI) testing procedure the relative flammability of a plastic material such as nylon, or polyethylene terephthalate is determined by measuring the minimum concentration of oxygen in a slowly rising mixture of oxygen and nitrogen that will just support combustion. Consequently the oxygen index expresses such minimum concentration of oxygen, expressed as volume percent, in a mixture of oxygen and nitrogen that will just support combustion.

The test is conducted by burning the material in a test column which is a heat resistant glass tube of 75mm minimum inside diameter and 450mm minimum height. At the bottom of the tube is a bed of glass beads about 100mm deep to mix and distribute the gas mixture. Within the glass tube used as the test column there is a specimen holder to support the treated plastic material while the apparatus is supplied with oxygen and nitrogen flow and control devices. The apparatus is also provided with an igniter which is a separate tube through which a combustible gas such as natural gas is used to ignite the test specimen. In the present testing program glass scrim supported molded sheets of nylon or polyethylene terephthalate ca. 0.2mm thick and about 25mm by 100mm in size are used as the test specimens which are prepared from nylon or polyethylene terephthalate powder and 1% to 20% by weight of the fire retardant additive; the data in the present work correspond to about 10% by weight of additive. As a result of the molding of the organic polymer, e.g., nylon or polyethyethylene terephthalate and the additive, an intimate admixture or melt of the molecules of the components is obtained.

In conducting the test, the specimen is clamped in the holder in the test column after which the desired initial concentration of oxygen is introduced to the ignited specimen. A number of tests are conducted to determine the minimum concentration of oxygen that will just support combustion.

The present condensation products are useful in combination with organic polymers generally to reduce combustibility. The normally flammable organic polymers which are rendered fire retardant in accordance with the invention may be natural or synthetic but are preferably a solid synthetic polymer, more preferably a nylon or ester type polymer. Examples of the polymer are cotton, wool, silk, paper, natural rubber, and paint, and also the high molecular weight homopolymers and copolymers of amides, e.g., (nylon 66 and nylon 6). Other polymers include esters such as polyethylene terephthalate, and polymers of other unsaturated aliphatic and aromatic hydrocarbons, e.g., ethylene, propylene, butylene, styrene, etc., and also acrylic polymers, e.g., polyacrylonitrile, polymethyl methacrylate, alkyd resins, as well as cellulose derivatives, e.g., cellulose acetate, methyl cellulose, etc. Still other polymers include epoxy resins, furan resins, isocyanate resins such as polyurethanes, melamine resins, vinyl resins such as polyvinyl acetate and polyvinyl chloride, resorcinol resins, synthetic rubbers such as polyisoprene, polybutadiene-acrylonitrile copolymers, butadiene-styrene polymers, butyl rubber, neoprene rubber, ABS resin and mixtures thereof. Since the compositions of the invention are unusually effective flame retardants they are normally combined in flame retarding proportions with the organic polymer at relatively low concentrations, e.g., about 1-20 wt. %, preferably about 3-15% based on additive plus the polymeric substrate, such as by milling, or impregnation, e.g., from a water or alcohol dispersion or solution or by dissolving or dispersing in the molten polymer before extrusion such as in the form of fibers or sheets. It should be noted that it is within the scope of the invention to incorporate such ingredients as dyes, pigments, stabilizers, antioxidants, antistatic agents and the like into the novel compositions.

The cyclic phosphorus compounds of the invention have a lesser tendency to cause cross linking of polymers than prior phosphonate flame retardants.

The following examples illustrate specific embodiments of the present invention but are not limitative of the scope of the invention.

EXAMPLE 1

A cyclic phosphorochloridite is first prepared as follows. A reaction vessel is charged with 272 grams (2.0 moles) of pentaerythritol, 567 grams of phosphorus trichloride, 0.1 gram of pyridine hydrochloride, and 272 grams of ortho-dichlorobenzene as a solvent. This mixture is warmed to 100° C in 2 hrs. and kept at 100°–105° C for 1 hour, giving a clear, colorless solution having a $^{31}P$ nmr signal at −149 ppm for the cyclic phosphorochloridite desired, 3,9-dichloro-2,4,8,10-tetraoxa-3,9-diphosphaspiro[5.5]undecane.

This intermediate is converted to the hydrogenphosphonate by dropwise addition of 184 grams (4 moles) of 97–100% formic acid over a 65 minute period. The temperature is maintained at about 25°–42° C during the addition. A stream of gaseous nitrogen is passed through the stirred reaction mixture until most of the by-product HCl and CO have been swept out. The reaction mixture is filtered to remove solids which are then washed with benzene, followed by acetonitrile and ether. The white solid hydrogen phosphonate product, $^{31}P$ nmr-6.4(d,$J_{PH}$ 696 cps), is 3,9-H-3,9-dioxa-2,3,8,10-tetraoxa-3,9-diphosphaspiro[5.5]undecane, having the formula shown below:

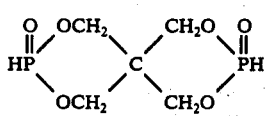

Analysis: Calcd. for $C_5H_{10}O_6P_2$ (percent): C, 26.33; H, 4.42; P, 27.16. Found: C, 26.17; H, 4.76; P, 26.77

The use of $PBr_3$ instead of $PCl_3$ leads to the same product.

EXAMPLE 2

The acetone derivative of the product of Example 1 is prepared in a one-step reaction from the phosphorochloridite precursor as follows: A solution of 3,9-dichloro-2,4,8,10-tetra-oxa-3,9-diphosphaspiro[5.5]undecane is prepared as in Example 1. Acetone, 348g (6.0 moles), is added, and then 202.4g (4.4 moles) of formic acid is added dropwise in 1 hr. and 40 minutes with cooling at 27°–40° C. The reaction mixture is warmed at 40°–52° C for one-half hr., filtered, and the resulting solid is washed with acetonitrile and acetone, giving 499g. of white solid, m.p. 207°–209° C (from glacial acetic acid and acetone), $^{31}P$ nmr −22.7 ppm, having the structure,

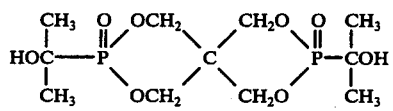

Analysis- Calcd. for $C_{11}H_{22}O_8P_2$: C, 38.37; H, 6.44; P, 17.99. Found: C, 38.20; H, 6.44; P, 17.90

Similar derivatives of methyl ethyl ketone, diethyl ketone, methyl propyl ketone, acetophenone, dibutyl ketone or of diphenyl ketone are obtained when these ketones are used in place of acetone in the above process. These ketone derivatives are also obtained when the hydrogen phosphonate is first prepared from a phosphorochloridite and formic acid and then the ketone added.

EXAMPLE 3

A solution of 2.0 moles of 2-chloro-5,5-dimethyl-1,3,2-dioxaphosphorinane in 200g. of 1,2-dichloroethane is stirred as 2.0 moles of formic acid is added dropwise at 20°–30° C. The product is then distilled twice, giving 217g. of colorless liquid, b.p. 98°–100°/0.15 mm., $^{31}P$ nmr-3.7 ppm (d, $J_{PH}$ 660 cps), which is the cyclic hydrogenphosphonate,

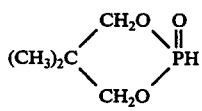

Analysis - Calcd. for $C_5H_{11}O_3P$: C, 40.01; H, 7.39; P, 20.63. Found C, 39.93; H, 7.34; P, 20.60

EXAMPLE 4

Phosphorus trichloride, 274.8 g (2.0 moles), is added dropwise to a stirred solution of 524 g. (2.0 moles) of 2,2-di(bromomethyl)-1,3-propanediol and 0.2g. of pyridine hydrochloride in 600 g. of benzene during 2.5 hrs. with enough warming to keep the temperature above 20° C. After several hours of stirring at room temperature, a $^{31}P$ nmr spectrum of the reaction mixture shows a peak for 90% of the phosphorus at −146.6 ppm for 2-chloro-5,5-bis(bromomethyl)-1,3,2-dioxaphosphorinane.

Stirring of the reaction mixture is continued as 106 g. (2.3 moles) of formic acid is added at room temperature during 2 hrs., followed by warming at 45° C. for 1.5 hrs. A solid product separates on cooling. This is recrystallized from benzene, giving 333 g. of white solid, m.p. 91°–96°, $^{31}P$ nmr −5.2 ppm (d, $J_{PH}$=695 cps), which is the cyclic hydrogenphosphonate, 5,5-bis(bromomethyl)-2-H-2-oxo-1,3,2-dioxaphosphorinane, having the structure,

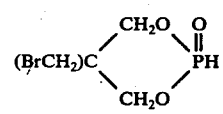

Similarly cyclic phosphorus compounds are obtained by the substitution of the above phosphorochloridite by other phosphorochloridites such as 2-chloro-5,5-dimethyl-1,3,2-dioxaphosphorinane, and 2-chloro-5-ethyl-5-methyl-1,3,2-dioxaphosphorinane, and 2-bromo-5,5-bis(chloromethyl)-1,3,2-dioxaphosphorinane, and 2-chloro-4-methyl-1,3,2-dioxaphosphorinane, and 2-chloro-5-phenyl-1,3,2-dioxaphosphorinane, and 2-chloro-5-(4-fluoro-3-bromophenyl)-1,3,2-dioxaphosphorinane,

EXAMPLE 5

A slurry of 0.2 mole of pentachlorobenzenesulfenyl chloride in 200 ml of benzene is added during 0.25 hr to a stirred solution of 0.2 mole of the product of Example 4 in 100 ml of benzene. The temperature increases from 25° to 40° C during the addition. The reaction mixture is warmed at reflux for 1 hr and then cooled and filtered. The solid that is isolated is recrystallized from chlorobenzene, giving a white solid, m.p. 187°–192°, $^{31}P$ nmr −17.0 ppm, which is 5,5-bis(bromomethyl)-2-oxo-2-pentachlorophenylthio-1,3,2-dioxaphosphorinane,

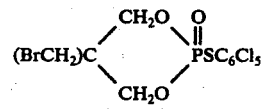

Analysis - Calcd. for $C_{11}H_8Br_2Cl_5O_3PS$: C, 22.45; H, 1.37; Br, 27.16; Cl, 30.13; P, 5.26; S, 5.45. Found: C, 22.58; H, 1.19; Br, 27.11; Cl, 29.99; P, 5.08; S, 5.47.

Similar products are formed when the sulfenyl chloride is chlorophenylsulfenyl chloride, nitrophenylsulfenyl chloride, bromophenylsulfenyl chloride, 2,4-nitrophenylsulfenyl chloride, chlorophenylsulfenyl chloride, or trichloromethylsulfenyl chloride.

EXAMPLE 6

Similarly, a mixture of 0.1 mole of the product of Example 1 when warmed in dimethylformamide with 0.2 mole of pentachlorobenzenesulfenyl chloride gives a white solid, m.p. 295°(dec.), which is 3,9-dioxo-3,9-bis(-pentachlorophenylthio)2,4,8,10-tetra-oxa-3,9-diphosphaspiro[5.5]undecane,

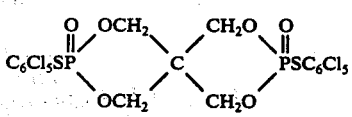

Analysis. — Calcd. for $C_{17}H_8Cl_{10}O_6P_2S_2$: C, 25.88; H, 1.02; Cl, 44.94; P, 7.85; S, 8.13. Found: C, 25.75; H, 1.04; Cl, 45.59; P, 7.87; S, 8.27.

Similar products are formed when the sulfenyl chloride is chlorophenyl sulfenyl chloride, nitrophenylsulfenyl chloride, bromophenylsulfenyl chloride, 2,4-dinitrophenylsulfenyl chloride, 4-chlorophenylsulfenyl chloride, or trichloromethylsulfenyl chloride.

EXAMPLE 7

Flame retardancy tests are conducted using typical compounds of the invention, specifically compounds of the above examples. These compounds do not burn readily subjected to heat and a flame, and also improve the flame retardant properties of polyamides, specifically nylon-6,6, and of polyethylene terephthalate at concentrations of 1–20% by weight, preferably 3–15% by weight, based upon the total mixture, such as by milling, or impregnation, or by dissolving or dispersing in the polymer in molten form before extrusion such as in the form of fibers or sheets. It should be noted that it is within the scope of the invention to incorporate such ingredients as dyes, pigments, stabilizers, antioxidants, antistatic agents and the like into the novel compositions.

Test data for certain compounds in the Oxygen Index Test are set forth below:

| FLAME RETARDANT DATA | |
| --- | --- |
| Compound of Example | OXYGEN INDEX (and % additive in total mixture) |
| 1 | 22.6 (5%) |
| 3 | 24.9 (10%) |
| 4 | 26.3 (10%) |
| 5 | 24.3 (10%) |
| 6 | 23.0 (10%) |

The other sulfenyl and ketone derivatives such as the product of Example 2 also have flame retardant properties, for polyethylene terephthalate and also polyamides, such as nylon 6.6.

What is claimed is:

1. A cyclic phosphorus compound having the formula

where Y is selected from the group consisting of

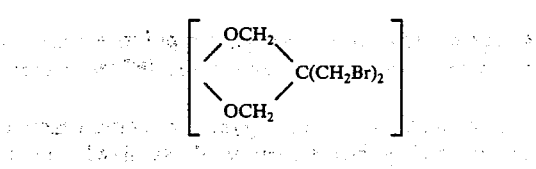

and

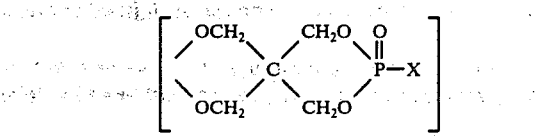

and where X is selected from the group consisting of
—S(R$_c$)

where R$_c$ is phenyl with 0 to 5 halogens, or phenyl with 0 to 2 nitro groups, or methyl with 0 to 3 chlorine atoms, and

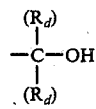

where R$_d$ is an alkyl radical of 1 to 4 carbon atoms, or phenyl.

2. Cyclic phosphorus compound as in claim 1 having the formula

where X is the group

where R$_c$ is phenyl with 0 to 5 halogens, or phenyl with 0 to 2 nitro groups, or methyl with 0 to 3 chlorine atoms.

3. Cyclic phosphorus compound as in claim 1 having the formula

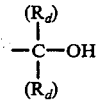

where X is the group

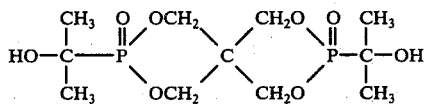

where R$_d$ is an alkyl radical of 1 to 4 carbon atoms, or phenyl.

4. The compound

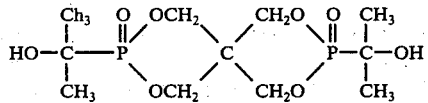

5. The compound

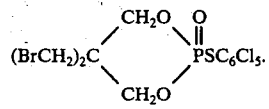

6. The compound

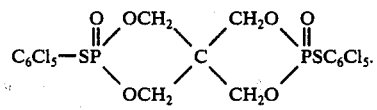

7. Process for the preparation of cyclic hydrogenphosphonate which comprises admixing at 10° C to 100°

C, formic acid with a cyclic phosphorochloridite having the formula

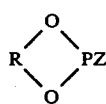

where R is an alkylene, or haloalkylene group of a 1,2-glycol having from 2 to 8 carbon atoms, or of a 1,3-glycol having from 3 to 8 carbon atoms, and Z is Cl or Br.

8. Process for the preparation of the compound

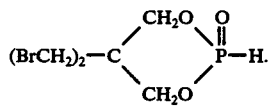

which comprises admixing at 10° to 100° C, formic acid with
2-chloro-5,5-bis(bromomethyl)-1,3,2-dioxaphosphorinane,

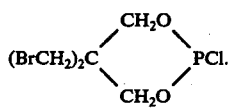

9. Process for the preparation of the compound

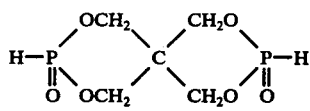

which comprises admixing at 10° to 100° C, formic acid with
3,9-dichloro-2,4,8,10-textraoxa-3,9-diphosphaspiro[5.5]undecane.

10. Process for the preparation of cyclic phosphorus compounds which comprises admixing at 10° to 100° C, formic acid with a phosphorochloridite selected from the group consisting of 2-chloro-5,5-dimethyl-1,3,2-dioxaphosphorinane, and 2-chloro-5-ethyl-5-methyl-1,3,2-dioxaphosphorinane, and 2-bromo-5,5-bis-(chloromethyl)-1,3,2-dioxaphosphorinane, and 2-chloro-4-methyl-1,3,2-dioxaphosphorinane, and 2-chloro-5-phenyl-1,3,2-dioxaphosphorinane, and 2-chloro-5-(4-fluoro-3-bromophenyl)-1,3,2-dioxaphosphorinane, 2-chloro-5,5-bis(bromomethyl)-1,3,2-dioxaphosphorinane, 3,9-dichloro-2,4,8,10-tetraoxa-3,9-diphosphaspiro[5.5]undecane.

11. Process for the preparation of a cyclic phosphorus compound which comprises admixing at 10° to 100° C, formic acid with a cyclic phosphorochloridite having the formula

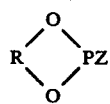

where R is an alkylene, or haloalkylene group of a 1,2-glycol having from 2 to 8 carbon atoms, or of a 1,3-glycol having from 3 to 8 carbon atoms, and Z is Cl or Br, and thereafter treating the reaction mixture with a sulfenyl chloride, $(R_c)$ SCl, where $R_c$ is phenyl with 0 to 5 halogen atoms, or phenyl with 0 to 2 groups, or methyl with 0 to 3 chlorine atoms.

12. Process for the preparation of a cyclic phosphorus compound which comprises admixing at 10° to 100° C, formic acid with a cyclic phosphorochloridite having the formula

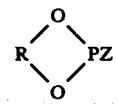

where R is an alkylene, or haloalkylene group of a 1,2-glycol having from 2 to 8 carbon atoms, or of a 1,3-glycol having from 3 to 8 carbon atoms, and Z is Cl or Br, and thereafter treating the reaction mixture with a ketone,

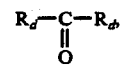

where $R_d$ is an alkyl radical of 1 to 4 carbon atoms, or phenyl.

13. Process for the preparation of a cyclic phosphorus compound which comprises admixing at 10° to 100° C, formic acid with a mixture of a cyclic phosphorochloridite having the formula

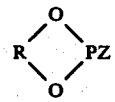

where R is an alkylene, or haloalkylene group of a 1,2-glycol having from 2 to 8 carbon atoms, or of a 1,3-glycol having from 3 to 8 carbon atoms, and Z is Cl or Br, and a ketone,

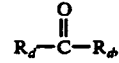

where $R_d$ is an alkyl radical of 1 to 4 carbon atoms or phenyl

14. The combination of an organic polymer together with a cyclic phosphorus compound as defined in claim 1.

15. The combination of an organic polymer together with a cyclic phosphorus compound as defined in claim 2.

16. The combination of an organic polymer together with a cyclic phosphorus compound as defined in claim 3.

17. The combination of an organic polymer together with a cyclic phosphorus compound as defined in claim 4.

18. The combination of an organic polymer together with a cyclic phosphorus compound as defined in claim 5.

19. The combination of an organic polymer together with a cyclic phosphorus compound as defined in claim 6.

20. The combination of polyethylene terephthalate together with a cyclic phosphorus compound as defined in claim 1.

21. The combination of polyamide resin together with a cyclic phosphorus compound as defined in claim 1.

22. The combination of polyethylene terephthalate together with a cyclic phosphorus compound as defined in claim 5.

23. The combination of polyethylene terephthalate together with a cyclic phosphorus compound as defined in claim 8.

* * * * *

UNITED STATES PATENT AND TRADEMARK OFFICE
CERTIFICATE OF CORRECTION

PATENT NO. : 4,070,336

DATED : January 24, 1978

INVENTOR(S) : Gail H. Birum

It is certified that error appears in the above-identified patent and that said Letters Patent are hereby corrected as shown below:

In Claim 2, at column 10, line 20, the formula for X reading
$$\begin{matrix} & O \\ & \| \\ X- & P-Y \end{matrix}$$
should read $-S(R_c)$.

Claim 3, at column 10, line 28 et seq. should read as follows: "Cyclic phosphorus compound as in Claim 1 having the formula
$$\begin{matrix} & O \\ & \| \\ X- & P-Y \end{matrix}$$
where X is the group
$$\begin{matrix} (R_d) \\ | \\ -C-OH \\ | \\ (R_d) \end{matrix}$$
where $R_d$ is an alkyl radical of 1 to 4 carbon atoms, or phenyl."

Signed and Sealed this

Second Day of January 1979

[SEAL]

Attest:

RUTH C. MASON
*Attesting Officer*

DONALD W. BANNER
*Commissioner of Patents and Trademarks*